United States Patent
Zimmermann et al.

(10) Patent No.: US 10,160,698 B2
(45) Date of Patent: Dec. 25, 2018

(54) USE OF MEMBRANE FOR OXIDATIVE-DEHYDROGENATION PROCESS

(71) Applicant: UOP LLC, Des Plaines, IL (US)

(72) Inventors: Joseph E. Zimmermann, Arlington Heights, IL (US); Bryan J. Egolf, Crystal Lake, IL (US); J. W. Adriaan Sachtler, Des Plaines, IL (US); Rajeswar Gattupalli, Buffalo Grove, IL (US); Charles M. Brabson, Humble, TX (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/663,348

(22) Filed: Jul. 28, 2017

(65) Prior Publication Data
US 2018/0118638 A1    May 3, 2018

Related U.S. Application Data

(60) Provisional application No. 62/414,572, filed on Oct. 28, 2016.

(51) Int. Cl.
| | | |
|---|---|---|
| C07C 5/32 | (2006.01) | |
| C07C 11/02 | (2006.01) | |
| B01J 23/40 | (2006.01) | |
| C01B 3/50 | (2006.01) | |
| B01D 53/68 | (2006.01) | |
| C07C 5/48 | (2006.01) | |
| C01B 3/26 | (2006.01) | |
| C02F 1/04 | (2006.01) | |

(52) U.S. Cl.
CPC .............. *C07C 5/325* (2013.01); *B01D 53/68* (2013.01); *B01J 23/40* (2013.01); *C01B 3/26* (2013.01); *C01B 3/501* (2013.01); *C01B 3/503* (2013.01); *C07C 5/48* (2013.01); *C07C 11/02* (2013.01); *C01B 2203/0277* (2013.01); *C01B 2203/0405* (2013.01); *C01B 2203/048* (2013.01); *C01B 2203/062* (2013.01); *C01B 2203/0822* (2013.01); *C01B 2203/0827* (2013.01); *C01B 2203/1247* (2013.01); *C02F 1/04* (2013.01)

(58) Field of Classification Search
CPC combination set(s) only.
See application file for complete search history.

(56) References Cited

U.S. PATENT DOCUMENTS

| | | | |
|---|---|---|---|
| 4,430,517 A | 2/1984 | Imai et al. | |
| 4,438,288 A | 3/1984 | Imai et al. | |
| 4,486,547 A | 12/1984 | Imai et al. | |
| 6,963,018 B2 | 11/2005 | Vasileiadis | |
| 7,495,138 B2 | 2/2009 | Crone | |
| 8,088,962 B2 | 1/2012 | Klanner | |
| 2004/0063989 A1* | 4/2004 | Hechler | C07C 51/215 558/320 |
| 2013/0158327 A1 | 6/2013 | Leonard | |
| 2014/0249339 A1 | 9/2014 | Simanzhenkov | |

FOREIGN PATENT DOCUMENTS

WO    2014138510 A1    9/2014

* cited by examiner

*Primary Examiner* — Randy Boyer

(57) ABSTRACT

A process is presented for the dehydrogenation of paraffins. The process utilizes heated air for the combustion of a fuel within the dehydrogenation reactor to provide the heat of reaction for oxidative dehydrogenation. The nitrogen in the air is utilized as a diluent. A paraffin feedstream is mixed with a fuel, and the fuel/paraffin feedstream is mixed with an oxidant air stream at the inlet of dehydrogenation reactor.

20 Claims, 1 Drawing Sheet

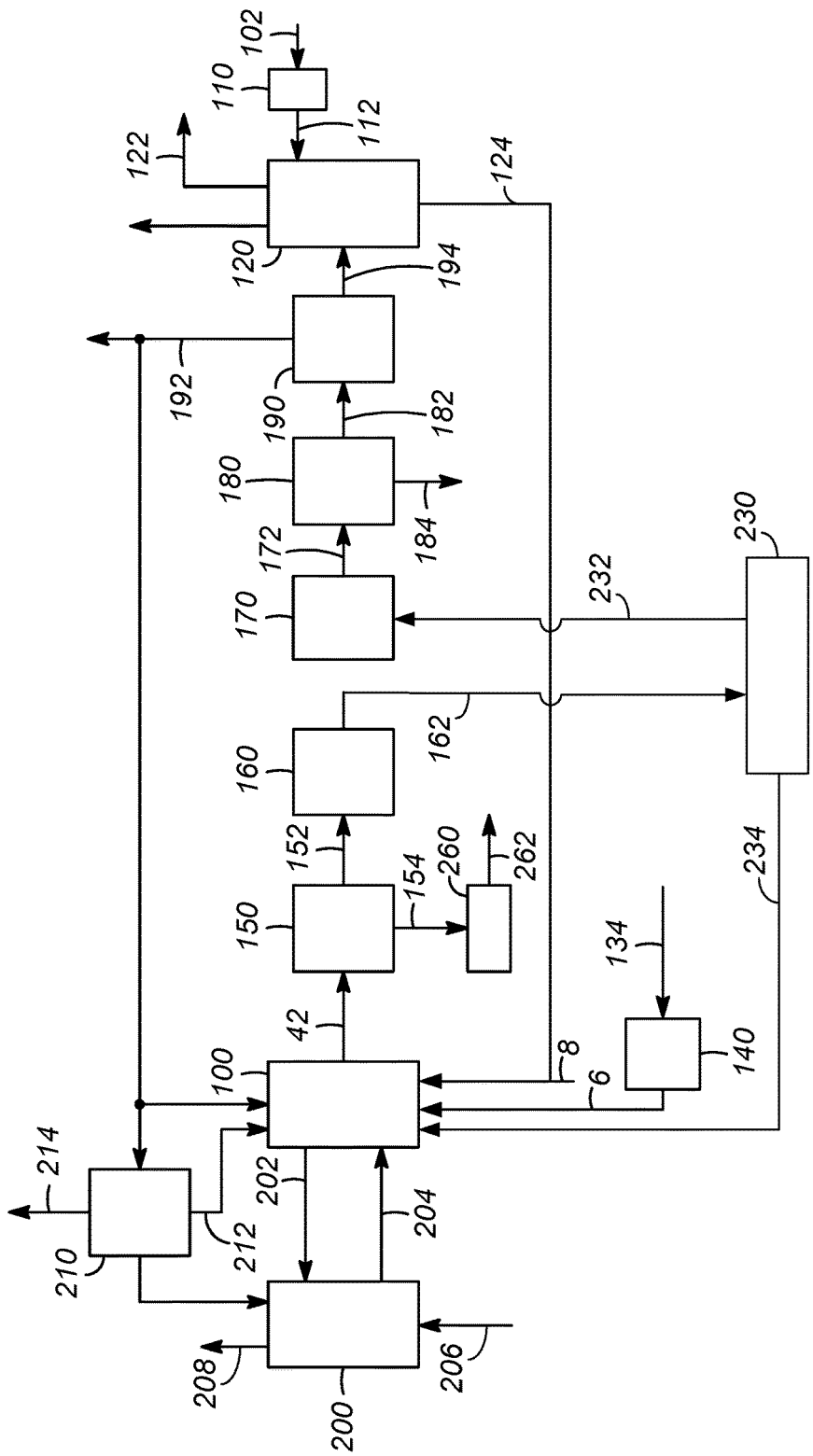

USE OF MEMBRANE FOR OXIDATIVE-DEHYDROGENATION PROCESS

CROSS-REFERENCE TO RELATED APPLICATION

This application claims priority from Provisional Application No. 62/414,572 filed Oct. 28, 2016, the contents of which cited application are hereby incorporated by reference in its entirety.

FIELD OF THE INVENTION

The field of this invention relates to the use of membrane separation for oxidative dehydrogenation of paraffins.

BACKGROUND

The dehydrogenation of paraffins is an important commercial hydrocarbon conversion process because of the existing and growing demand for olefins for the manufacture of various chemical products such as detergents, high octane gasolines, and oxygenated gasoline blending components, pharmaceutical products, plastics, synthetic rubbers, and other products which are well known to those skilled in the art. One example of this process is the dehydrogenation of propane to produce propylene which can be polymerized to polypropylene, a common plastic.

Those skilled in the art of paraffin conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al) discusses a dehydrogenation process and catalyst for use therein.

In existing oxidative-dehydrogenation processes for paraffin dehydrogenation, a mixture of steam and oxygen is used to combust the hydrogen partially to generate heat and increase the temperature of hydrogen and paraffin to the designed reaction temperature. The ratio of oxygen, hydrogen and paraffin needs to be controlled to avoid explosive mixture. So conventionally excess paraffins are added as diluents for dehydrogenation of paraffins. However, the addition of paraffin as diluents requires additional external heating or additional oxygen to maintain the inlet temperatures and makes the process potentially uneconomical. Alternatively, air is used instead of pure oxygen to partially combust the hydrogen. The nitrogen in the air may act as diluent to keep the mixture of oxygen, paraffin and hydrogen mixture outside the explosive unit. Still, nitrogen needs to be separated from the hydrogen rich product stream produced in the dehydrogenation reaction. The conventional separation techniques for separation of nitrogen from hydrogen are complex and require additional equipments like compressors for compression of nitrogen, contribute substantially to the operating costs. While technology has improved in the production of olefins through dehydrogenation processes, there is still room for improving the economics and the process to increase production and decrease cost.

Further, the catalysts used for the dehydrogenation of hydrocarbons are susceptible to deactivation over time. Deactivation will typically occur because of an accumulation of deposits that block active pore sites or catalytic sites on the catalyst surface. Therefore, there is a need for a new process configuration to separate nitrogen from hydrogen rich product stream produced by the dehydrogenation reaction in an economical way that can consequently enable a recycle of the separated hydrogen to the reactor to control the rate of coking on the dehydrogenation catalyst.

SUMMARY

An embodiment of the invention is a process for dehydrogenation of paraffins comprising passing a paraffin stream to a dehydrogenation reactor to generate a process stream comprising olefins. The process stream comprising olefins is subsequently passed to a low pressure separator to generate a water stream and a process stream with reduced water content. The process stream with reduced water content is passed to a compressor to generate a compressed process stream. The compressed water stream is passed to a membrane separation unit to generate a hydrogen rich stream and a process stream with reduced hydrogen content. The hydrogen rich stream is subsequently passed to the dehydrogenation reactor.

Another embodiment of the invention is a process for oxidative dehydrogenation of paraffins comprising pretreating a paraffins stream to generate a cleaned paraffin stream. The cleaned paraffin stream is passed to an oxidative dehydrogenation reactor. A fuel stream is passed to the oxidative dehydrogenation reactor. A heated air stream is passed to the oxidative dehydrogenation reactor, wherein the air, fuel and paraffin are reacted to generate a process stream comprising olefins. The process stream comprising olefins is subsequently passed to a low pressure separator to generate a water stream and a process stream with reduced water content. The process stream with reduced water content is passed to a compressor to generate a compressed process stream. The compressed water stream is passed to a membrane separation unit to generate a hydrogen rich stream and a process stream with reduced hydrogen content. The hydrogen rich stream is subsequently passed to the oxidative dehydrogenation reactor. The process stream with reduced hydrogen content is passed to a chloride treater to generate a process stream with reduced chloride. The process stream with reduced chloride is passed to an acid gas treater to generate a process stream with reduced acid gases. The process stream with reduced acid gases is passed to a light gas separation unit to generate a light gas comprising hydrogen and a second process stream comprising olefins.

The present invention seeks to provide a streamlined process that enables use of nitrogen as diluents for dehydrogenation of paraffins. The present invention eliminates the need of costly air separation equipments to produce oxygen for dehydrogenation of paraffins. These and other features, aspects, and advantages of the present invention will become better understood upon consideration of the following detailed description, drawing and appended claims.

BRIEF DESCRIPTION OF THE DRAWING

The FIGURE is a flow scheme for the process of the present invention.

DETAILED DESCRIPTION

Dehydrogenation processes are important sources for the conversion of paraffins to olefins. The ratio of oxygen, hydrogen and paraffin in an oxidative dehydrogenation reaction must be controlled to avoid an explosive mixture. This is generally done by addition of a diluent. Air rather than pure oxygen can be used to partially combust the hydrogen in an oxidative dehydrogenation reaction. The nitrogen in air may be used as diluents to keep the oxygen, paraffin and hydrogen mixture outside of the explosive limit. However, nitrogen is not condensable and remains part of the product stream as this stream moves through compression, scrubbing, and absorption sections, and it drives the equipment size, the piping size, as well as the overall design considerations. The present invention provides an efficient method to separate the nitrogen from the hydrogen rich product stream produced by the dehydrogenation reaction.

A drawback of providing nitrogen in air as diluent is the need to separate the nitrogen from hydrogen rich product stream produced by dehydrogenation reaction. The separation of the nitrogen from the hydrogen rich product stream cannot be easily done by fractionation or cryogen separation as conventionally practiced in non-oxidative dehydrogenation process. Separation by pressure swing absorption would require excessive compression of the nitrogen and the remaining reactor effluent from the hydrogen and therefore is uneconomical.

The present invention provides a method to separate nitrogen from the hydrogen-rich product stream produced by the dehydrogenation process by use of a membrane separation unit. The hydrogen-rich product stream may be compressed to a suitably high pressure and sent to the membrane separation unit. The membrane separation unit separates the hydrogen from the nitrogen and the hydrogen is delivered as a relatively low pressure is recycled back at low pressure without any additional compression. The nitrogen, remaining hydrogen and the paraffin-olefin reactor effluent at relatively high pressure may be easily separated subsequently by fractionation. The remaining stream comprising nitrogen, the hydrocarbons and some hydrogen can be passed to a light gas separation unit. The light gas separation unit can utilize cold box technology to condense the C4 hydrocarbons, and generates a liquid phase stream comprising n-butane and n-butene. The liquid phase stream is passed to a butane extraction column to generate a butane stream comprising n-butane and a butene stream comprising n-butene. The extraction column uses a solvent separation system, with a solvent passed to the extraction column to preferentially absorb the olefin. The butane stream can be recycled back to the non-oxidative dehydrogenation reactor to generate more butenes.

A benefit of the present invention is with the use of nitrogen rather than paraffin as a diluent allows improvement in process economics. An additional benefit of the present invention is elimination of expensive air-separation system to produce oxygen that further improves the process economics.

A general understanding of the process for dehydrogenation of paraffins can be obtained by reference to the FIGURE. The FIGURE has been simplified by the deletion of a large number of apparatuses customarily employed in a process of this nature, such as vessel internals, temperature and pressure controls systems, flow control valves, recycle pumps, etc. which are not specifically required to illustrate the performance of the invention. Furthermore, the illustration of the process of this invention in the embodiment of a specific drawing is not intended to limit the invention to specific embodiments set out herein.

The present invention, as shown in the FIGURE, includes a reactor system 100 for a process for dehydrogenation of paraffins to olefins. The reactor system 100 may be a dehydrogenation reactor. An exemplary dehydrogenation reactor may be an oxidative dehydrogenation reactor. A feed stream in line 8 having a paraffin stream and a fuel stream comprising a fuel gas is passed to the oxidative dehydrogenation reactor 100 to generate a process stream comprising olefins. The fuel gas can comprise a mixture of light combustible gases useful primarily for heating, and can include a mixture of hydrogen, methane, carbon monoxide and other light hydrocarbons. The paraffin stream is pretreated to generate a cleaned paraffin stream. The cleaned paraffin stream is passed to the oxidative dehydrogenation reactor 100. The dehydrogenation reactor 100 comprises a catalyst, and is operated at dehydrogenation reaction conditions. Air in line 134 is heated in a fired heater 140 to generate the heated air stream in line 6. The heated air stream may be the oxidant and is passed to the oxidative dehydrogenation reactor 100. The heated air, fuel and paraffin are reacted to generate a process stream comprising olefins in line 42. The paraffin stream in line 8 may be heated before it is passed to the dehydrogenation reactor. The paraffin stream may be propane or butane. The partial pressure of the oxidant air can be controlled by the addition of steam to the dehydrogenation reactor. The process stream comprising olefins in line 42 is passed to a low pressure separator 150 to generate a process stream with reduced water content in line 152 and a water stream in line 154. The water stream in line 154 is passed to a waste water treatment unit 260 to recover steam in line 262. The process stream with reduced water content in line 152 is passed to a compressor 160 to generate a compressed process stream in line 162. The compressed process stream in line 162 is passed to a membrane separation unit 230 to generate a hydrogen rich stream in line 234 and a process stream with reduced hydrogen content in line 232. Membrane separation technology can include the use of zeolites, microporous ceramics, microporous metals, dense ceramics, and dense metals. On example of a metal membrane is a palladium membrane of a ceramic substrate. For low temperature membrane separation of hydrogen, the membranes can include polyimides, or imidazole-based polymer membranes. For lower temperature separation, the process stream can be passed through a heat exchanger to bring the process stream temperature down to levels to prevent damage to the polymeric membranes.

The hydrogen rich stream in line 234 is passed to the dehydrogenation reactor 100. The hydrogen recycled to the reactor 100 is used as a fuel to combust and provide the heat of reaction for the oxidative dehydrogenation process. The process stream with reduced hydrogen content is passed to a chloride treater 170 to remove chlorides and generate a second process stream with reduced chloride in line 172. The second process stream with reduced chloride in line 172 is passed to an acid gas treater 180 to remove acid gases in line 184 and generate a third process stream with reduced acid gases in line 182. An acid gas treater may be an amine unit. The third process stream with reduced acid gases in line 182 is passed to a light gas separation unit 190 to generate a light gas comprising methane, and other light gases, in line 192 for recycle and purge, and a fourth process stream comprising olefins in line 194. The methane in line 192 is mixed with the paraffin feed in line 8 and fed to the dehydrogenation reactor 100. The fourth process stream comprising olefins in line 194 is passed to a product separation unit 120 to generate an olefin product stream in line 122 and other unconverted paraffins in line 124. The unconverted paraffins in line 124 are passed to the feed stream in line 8 and recycled to the dehydrogenation reactor 100.

A paraffin stream in line 102 is treated in a feed treatment unit 110, to generate a treated feed in line 112. The treated feed in line 112 is passed through the product separation unit 120 and generates a feed stream in line 8 made up of recycled paraffin and new paraffin. The product separation unit includes a cold-box separator and fractionation section.

An exemplary reactor system includes a moving bed reactor system, and the catalyst in the system flows through the reactor system 100, and a spent catalyst stream in line 202 is passed to a catalyst regeneration unit 200. A regenerated catalyst stream in line 204 is returned to the reactor system 100. Air in line 206 is passed to the catalyst regeneration unit 200 to burn the carbon in the spent catalyst stream in line 202. A flue gas stream in line 208 exits the catalyst regeneration unit 200 when the carbon is burned off. The residual hydrogen in line 192 can be purified in a pressure swing absorber 210 to provide a stream of higher concentration hydrogen for the process in line 212, and excess hydrogen 214 can be passed to other process units within a chemical plant.

The oxidant stream in line 6 passed to the dehydrogenation reactor 10 combusts the fuel to generate heat. The amount of oxidant and fuel is set to raise the temperature in the reactor unit 100 to a temperature between 540° C. and 700° C. The reaction system 100 can include one or more reactor units. The reactor units can be stacked with the reactants and catalyst flowing from one reactor unit to another. The reactor units can also be fixed bed reactors, and can be positioned in a side by side orientation. The reactor units can be arranged in series, and can be positioned in any convenient manner, in particular in a manner that facilitates the transfer of reactants between reactor units, and provides for access to admit flows or withdraw process streams.

A preferred fuel is hydrogen, and with hydrogen generated by the process, the fuel is generated as the process stream passes from one reactor unit to the subsequent reactor unit within the series of reactor units.

The present invention can utilize fixed bed reactors or moving bed reactors. The oxidative dehydrogenation reactor may be a moving bed reactor with a catalyst inlet and a catalyst outlet. A preferred mode is for the use of moving bed reactors, with fresh regenerated catalyst passed to the first reactor unit. The catalyst from the first reactor unit is passed to the second reactor unit, and the catalyst continues flowing through the series of reactor units until the last reactor unit. The catalyst exiting the last reactor unit is sent to the regeneration unit 200, where the catalyst is regenerated and recycled to the first reactor unit. The catalyst regeneration unit includes an inlet in fluid communication with the oxidative dehydrogenation reactor catalyst outlet and an outlet in fluid communication with the oxidative dehydrogenation reactor catalyst inlet.

The process can further include reactor units which comprise a plurality of reactor beds. In this embodiment, each reactor bed within each reactor unit has an inlet for the admission of a fresh stream of oxidant, and the oxidant stream to each reactor unit is split into a plurality of portions with each portion fed to a separate reactor bed.

The process of the present invention can be used for different paraffin streams, and is preferably operated at conditions such that the paraffin is in the vapor phase. A preferred paraffin feedstream is propane or butane.

The dehydrogenation reaction conditions include contacting the paraffin with a dehydrogenation catalyst at an elevated temperature. The dehydrogenation catalyst comprises a metal on a support. Operating conditions for the preferred dehydrogenation zone, comprising the dehydrogenation reactor units, of this invention will usually include an operating temperature in the range of from 500° C. to 700° C., an operating pressure from 100 kPa to 450 kPa (absolute) and a liquid hourly space velocity of from about 0.5 to about 50 for each catalyst bed. The preferred operating temperature will be within the range of from about 540° C. to 660° C., and the preferred operating pressure is 100 kPa to 250 kPa (absolute). A more preferred operating conditions include a temperature is 580° C. to 645° C., an operating pressure from 100 kPa to 170 kPa (absolute), and preferably operating conditions such that the effluent stream from each reactor unit is at a temperature of above 500° C., and most preferably at 580° C., with an operating temperature between 600° C. to 645° C. The temperature can be controlled by the flow of oxidant to the reactor units. When the effluent stream temperature is too high, the oxidant can be used as a quench to bring the inlet temperature of the feed and oxidant to the next reactor to below 580° C. The heated air stream to each reactor bed is sufficient to combust the fuel and heat the feed stream sufficiently to provide for the effluent stream exiting at a temperature of at least 580° C.

The feedstream comprising fuel and paraffin has a molar ratio from 0 to 1, with a preferred ratio between 0.1 and 0.7, and a more preferred ratio between 0.2 and 0.5.

The preferred dehydrogenation catalyst is comprised of a Group VIII metal, and preferably a platinum group component, preferably platinum, a tin component and an alkali metal component with a porous inorganic carrier material. Another metal that can be used is chromium. Other catalytic compositions may be used within this zone if desired. The preferred catalyst contains an alkali metal component chosen from cesium, rubidium, potassium, sodium and lithium. The preferred alkali metal is normally chosen from cesium and potassium. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions are available in patents, such as those cited above, and other standard references (U.S. Pat. Nos. 4,486,547 and 4,438,288).

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for the dehydrogenation of paraffins comprising passing a paraffin stream to a dehydrogenation reactor to generate a process stream comprising olefins; passing the process stream comprising olefins to a low a low pressure separator to generate a water stream and a process stream with reduced water content; passing the process stream with reduced water content to a compressor to generate a compressed process stream; passing the compressed process stream to a membrane separation unit to generate a hydrogen rich stream and a process stream with reduced hydrogen content; and passing the hydrogen rich stream to the dehydrogenation reactor. An embodiment of the invention is one, any or all of prior embodiments in this paragraph up through the first embodiment in this paragraph wherein the dehydrogenation reactor is an oxidative dehydrogenation reactor, further comprising passing a fuel stream, comprising a fuel gas, to the oxidative dehydrogenation reactor; and passing a heated air stream to the oxidative dehydrogenation reactor, wherein the air, fuel, and paraffin are reacted to generate the process stream comprising olefins. An embodiment of the invention is one, any or all of prior embodiments in this paragraph up through the first embodiment in this paragraph wherein the paraffin stream is heated before passing to the dehydrogenation reactor. An embodiment of the invention is one, any or all of prior embodiments in this paragraph up through the first embodiment in this paragraph wherein the paraffin is propane or butane. An embodiment of the invention is one, any or all of prior embodiments in this paragraph up through the first embodiment in this paragraph further comprising passing steam to the dehydrogenation reactor. An embodiment of the invention is one, any or all of prior embodiments in this paragraph up through the first embodiment in this paragraph further comprising passing the process stream with reduced hydrogen to a chloride treater to generate a second process stream with reduced chloride; passing the second process stream with reduced chloride to an acid gas treater to generate a third process stream with reduced acid gases; and passing the third process stream with reduced acid gases to a light gas separation unit to generate a light gas comprising methane and a fourth process stream comprising olefins. An embodiment of the invention is one, any or all of prior embodiments in this paragraph up through the first embodiment in this paragraph further comprising passing the fourth process stream comprising olefins to a product separation unit to generate an olefin product stream and a stream of unconverted paraffins; and recycling the stream of unconverted paraffins to the dehydrogenation reactor. An embodiment of the invention is one, any or all of prior embodiments in this paragraph up through the first embodiment in this paragraph wherein the acid gas treater is an amine unit. An embodiment of the invention is one, any or all of prior embodiments in this paragraph up through the first embodiment in this paragraph wherein the fuel gas is hydrogen. An embodiment of the invention is one, any or all of prior embodiments in this paragraph up through the first embodiment in this paragraph wherein the dehydrogenation reaction conditions include contacting the paraffin with a dehydrogenation catalyst at an elevated temperature, wherein the catalyst comprises a metal on support. An embodiment of the invention is one, any or all of prior embodiments in this paragraph up through the first embodiment in this paragraph wherein the heated air stream to each reactor bed is sufficient to combust the fuel and heat the feed stream sufficiently to provide for the effluent stream exiting at a temperature of at least 580° C. An embodiment of the invention is one, any or all of prior embodiments in this paragraph up through the first embodiment in this paragraph wherein the reaction conditions includes a pressure less than 450 kPa (absolute). An embodiment of the invention is one, any or all of prior embodiments in this paragraph up through the first embodiment in this paragraph wherein the reaction conditions includes a pressure less than 250 kPa (absolute). An embodiment of the invention is one, any or all of prior embodiments in this paragraph up through the first embodiment in this paragraph wherein the oxidative dehydrogenation reactor is a moving bed reactor, having a catalyst inlet and catalyst outlet. An embodiment of the invention is one, any or all of prior embodiments in this paragraph up through the first embodiment in this paragraph further comprising a catalyst regeneration unit having an inlet in fluid communication with the oxidative dehydrogenation reactor catalyst outlet, and an outlet in fluid communication with the oxidative dehydrogenation reactor catalyst inlet.

A second embodiment of the invention is a process for the oxidative dehydrogenation of paraffins comprising pretreating a paraffins stream to generate cleaned paraffins stream; passing the cleaned paraffins stream to an oxidative dehydrogenation reactor; passing a fuel stream to the oxidative dehydrogenation reactor; passing a heated air stream to the oxidative dehydrogenation reactor, wherein air, fuel and paraffin are reacted to generate a first process stream comprising olefins; passing the first process stream comprising olefins to a low a low pressure separator to generate a water stream and a process stream with reduced water content; passing the process stream with reduced water content to a compressor to generate a compressed process stream; passing the compressed process stream to a membrane separation unit to generate a hydrogen rich stream and a process stream with reduced hydrogen content; passing the hydrogen rich stream to the oxidative dehydrogenation reactor; passing the process stream with reduced hydrogen content to a chloride treater to generate a process with reduced chloride; passing the process stream with reduced chloride to an acid gas treater to generate a process stream with reduced acid gases; and passing the process stream with reduced acid gases to a light gas separation unit to generate a light gas comprising hydrogen and a second process stream comprising olefins. An embodiment of the invention is one, any or all of prior embodiments in this paragraph up through the second embodiment in this paragraph wherein the dehydrogenation reaction conditions include contacting the paraffin with a dehydrogenation catalyst at an elevated temperature, wherein the catalyst comprises a metal on a support. An embodiment of the invention is one, any or all of prior embodiments in this paragraph up through the second embodiment in this paragraph wherein the heated air stream to each reactor bed is sufficient to combust the fuel and heat the feed stream sufficiently to provide for the effluent stream exiting at a temperature of at least 580° C. An embodiment of the invention is one, any or all of prior embodiments in this paragraph up through the second embodiment in this paragraph wherein the reaction conditions includes a pressure less than 450 kPa.

Without further elaboration, it is believed that using the preceding description that one skilled in the art can utilize the present invention to its fullest extent and easily ascertain the essential characteristics of this invention, without departing from the spirit and scope thereof to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

The invention claimed is:

1. A process for the dehydrogenation of paraffins comprising:
   passing a paraffin stream to a dehydrogenation reactor to generate a process stream comprising olefins;
   passing the process stream comprising olefins to a low pressure separator to generate a water stream and a process stream with reduced water content;
   passing the process stream with reduced water content to a compressor to generate a compressed process stream;
   passing the compressed process stream to a membrane separation unit to generate a hydrogen rich stream and a process stream with reduced hydrogen content;

passing the hydrogen rich stream to the dehydrogenation reactor;
passing the process stream with reduced hydrogen to a chloride treater to generate a second process stream with reduced chloride;
passing the second process stream with reduced chloride to an acid gas treater to generate a third process stream with reduced acid gases; and
passing the third process stream with reduced acid gas to a light gas separation unit to generate a light gas comprising methane and a fourth process stream comprising olefins.

2. The process of claim 1 wherein the dehydrogenation reactor is an oxidative dehydrogenation reactor, further comprising:
passing a fuel stream, comprising a fuel gas, to the oxidative dehydrogenation reactor; and
passing a heated air stream to the oxidative dehydrogenation reactor, wherein the air, fuel and paraffin are reacted to generate the process stream comprising olefins.

3. The process of claim 1 wherein the paraffin stream is heated before passing to the dehydrogenation reactor.

4. The process of claim 1 wherein the paraffin is propane or butane.

5. The process of claim 1 further comprising passing steam to the dehydrogenation reactor.

6. The process of claim 1 further comprising:
passing the fourth process stream comprising olefins to a product separation unit to generate an olefin product stream and a stream of unconverted paraffins; and
recycling the stream of unconverted paraffins to the dehydrogenation reactor.

7. The process of claim 1 wherein the acid gas treater is an amine unit.

8. The process of claim 2 wherein the fuel gas is hydrogen.

9. The process of claim 2 further comprising:
passing the process stream with reduced hydrogen content to a chloride treater to generate a second process stream with reduced chloride;
passing the second process stream with reduced chloride to an acid gas treater to generate a third process stream with reduced acid gases;
passing the third process stream with reduced acid gas to a light gas separation unit to generate a fuel gas stream comprising methane and nitrogen and a fourth process stream comprising olefins;
passing the fuel gas stream to a pressure swing absorber to generate a fuel gas stream with reduced nitrogen content; and
passing the fuel gas stream to the dehydrogenation reactor.

10. The process of claim 1 wherein the dehydrogenation reaction conditions include contacting the paraffin with a dehydrogenation catalyst at an elevated temperature, wherein the catalyst comprises a metal on a support.

11. The process of claim 2 wherein the heated air stream to each reactor bed is sufficient to combust the fuel and heat the feed stream sufficiently to provide for the effluent stream exiting at a temperature of at least 580° C.

12. The process of claim 1 wherein the reaction conditions includes a pressure less than 450 kPa (absolute).

13. The process of claim 12 wherein the reaction conditions include a pressure less than 250 kPa (absolute).

14. The process of claim 1 wherein the dehydrogenation reactor is a moving bed reactor, having a catalyst inlet and a catalyst outlet.

15. The process of claim 14 further comprising passing catalyst through the dehydrogenation reactor catalyst outlet to an inlet of a catalyst regeneration unit, and passing catalyst from an outlet of the catalyst regeneration unit to the dehydrogenation reactor catalyst inlet.

16. A process for the oxidative dehydrogenation of paraffins comprising:
pretreating a paraffins stream to generate a cleaned paraffin stream;
passing the cleaned paraffin stream to an oxidative dehydrogenation reactor;
passing a fuel stream to the oxidative dehydrogenation reactor;
passing a heated air stream to the oxidative dehydrogenation reactor, wherein the air, fuel and paraffin are reacted to generate a first process stream comprising olefins;
passing the first process stream comprising olefins to a low pressure separator to generate a water stream and a process stream with reduced water content;
passing the process stream with reduced water content to a compressor to generate a compressed process stream;
passing the compressed process stream to a membrane separation unit to generate a hydrogen rich stream and a process stream with reduced hydrogen content;
passing the hydrogen rich stream to the oxidative dehydrogenation reactor;
passing the process stream with reduced hydrogen content to a chloride treater to generate a process stream with reduced chloride;
passing the process stream with reduced chloride to an acid gas treater to generate a process stream with reduced acid gases; and
passing process stream with reduced acid gases to a light gas separation unit to generate a light gas comprising hydrogen and a second process stream comprising olefins.

17. The process of claim 16 wherein the dehydrogenation reaction conditions include contacting the paraffin with a dehydrogenation catalyst at an elevated temperature, wherein the catalyst comprises a metal on a support.

18. The process of claim 16 wherein the heated air stream to each reactor bed is sufficient to combust the fuel and heat the feed stream sufficiently to provide for the effluent stream exiting at a temperature of at least 580° C.

19. The process of claim 16 wherein the reaction conditions includes a pressure less than 450 kPa (absolute).

20. A process for the dehydrogenation of paraffins comprising:
passing a paraffin stream and a fuel stream comprising a fuel gas to an oxidative dehydrogenation reactor wherein the air, fuel, and paraffin are reacted to generate a process stream comprising olefins;
passing the process stream comprising olefins to a low pressure separator to generate a water stream and a process stream with reduced water content;
passing the process stream with reduced water content to a compressor to generate a compressed process stream;
passing the compressed process stream to a membrane separation unit to generate a hydrogen rich stream and a process stream with reduced hydrogen content;
passing the hydrogen rich stream to the dehydrogenation reactor;

passing the process stream with reduced hydrogen content to a chloride treater to generate a second process stream with reduced chloride;

passing the second process stream with reduced chloride to an acid gas treater to generate a third process stream with reduced acid gases;

passing the third process stream with reduced acid gas to a light gas separation unit to generate a fuel gas stream comprising methane and nitrogen and a fourth process stream comprising olefins;

passing the fuel gas stream to a pressure swing absorber to generate a fuel gas stream with reduced nitrogen content; and passing the fuel gas stream to the dehydrogenation reactor.

\* \* \* \* \*